United States Patent [19]

Norman et al.

[11] Patent Number: 5,740,221
[45] Date of Patent: Apr. 14, 1998

[54] AIRBAG INFLATOR X-RAY INSPECTION APPARATUS WITH ROTATING ENTRY AND EXIT DOORS

[75] Inventors: Kerry J. Norman, Brigham; Brian L. Baxter, Hooper; Kenneth D. Fowler, Farmington; Daren L. Sagers; Michael J. Hill, both of Logan; Jeffery P. England, Clinton, all of Utah

[73] Assignee: Morton International, Inc., Chicago, Ill.

[21] Appl. No.: 738,627

[22] Filed: Oct. 29, 1996

[51] Int. Cl.⁶ ............................................. G01N 23/04
[52] U.S. Cl. ................................................. 378/58; 378/57
[58] Field of Search ........................... 378/57, 58, 68, 378/69

[56] References Cited

U.S. PATENT DOCUMENTS

| | | | |
|---|---|---|---|
| 925,605 | 6/1909 | Solliday. | |
| 3,125,232 | 3/1964 | Brinkman et al. | 214/17 |
| 3,384,235 | 5/1968 | Schulze et al. | 209/73 |
| 4,020,346 | 4/1977 | Dennis | 250/358 R |
| 4,047,624 | 9/1977 | Dorenbos | 214/17 B |
| 4,205,216 | 5/1980 | Douglas | 219/121 L |
| 4,239,969 | 12/1980 | Haas et al. | 250/359 |
| 4,252,413 | 2/1981 | Nablo | 250/310 |
| 4,466,791 | 8/1984 | Jacobs et al. | 432/23 |
| 4,879,735 | 11/1989 | Owens | 378/57 |
| 5,131,797 | 7/1992 | Christiansen et al. | 414/219 |
| 5,202,932 | 4/1993 | Cambier et al. | 378/57 |
| 5,364,225 | 11/1994 | Hecht et al. | 414/786 |
| 5,367,552 | 11/1994 | Peschmann | 378/57 |
| 5,467,379 | 11/1995 | Bybee et al. | 378/58 |
| 5,491,737 | 2/1996 | Yarnall et al. | 378/58 |
| 5,615,244 | 3/1997 | Dykster et al. | 378/57 |

Primary Examiner—Don Wong
Attorney, Agent, or Firm—Steven C. Benjamin; Gerald K. White

[57] ABSTRACT

An x-ray inspection apparatus designed for safe, efficient, simple and rapid inspection of assembled automotive airbag inflators to detect the presence of defects in construction. The apparatus includes a lead-lined cabinet having spaced apart entry and exit openings and a central inspection space intermediate thereto which houses a continuous source of x-rays and an x-ray visual imaging system for converting x-radiation into a visible image that can be compared to a standard in order to determine whether the inflator has been properly constructed. The apparatus also includes a conveyor for moving inflators into and out of the x-ray cabinet. The entry and exit sections of the x-ray cabinet are sealed with respective single rotating doors. Each rotating door includes a rotatable cylindrical drum having only one opening in the sidewall of the drum configured to receive an inflator. The rotatable drum is housed in a separate lead-lined door cabinet attached to respective entry and exit sections of the x-ray cabinet. The door cabinet includes two spaced sidewalls having openings formed therein which are configured to receive an inflator. In operation, when the entry door is positioned upstream, an inflator enters the drum and is stopped in the interior of the drum. The drum door then rotates 180° with the door opening in the downstream position and the inflator is released and exits the door to the inside of the x-ray cabinet. The exit door works in the same manner. The rotary doors effectively seal x-radiation from exiting the x-ray cabinet into the surrounding area in all rotative positions, thereby effectively shielding line workers from harmful x-radiation during x-ray and transfer operations.

22 Claims, 5 Drawing Sheets

AIRBAG INFLATOR X-RAY INSPECTION APPARATUS WITH ROTATING ENTRY AND EXIT DOORS

FIELD OF THE INVENTION

The present invention relates to an x-ray inspection apparatus for inspecting articles, including automotive airbag inflators, and more particularly to a conveyor fed x-ray inspection apparatus with rotating entry and exit doors that provide for better shielding of personnel from radiation.

BACKGROUND OF THE INVENTION

A number of types of inflation devices, commonly referred to as gas generators or inflators, are well known for inflation of vehicle inflatable restraint cushions, commonly referred to as airbags.

Air bag inflators, for instance, driver side, passenger side, and side impact inflators, generally comprise a hermetically sealed ported metal body that houses, in various arrangements, an electric ignition squib, an igniter, a gas generant, and a filter. The airbag inflator is typically mounted together with a folded air bag in a reaction canister that is then mounted in a hidden vehicle compartment.

In the event of a collision, the inflator receives an electric activation signal from a crash sensor, which senses the sudden deceleration of the vehicle indicative of a collision, to activate the inflator. Upon inflator activation, the ignition squib fires and ignites the igniter, which, in turn, ignites the gas generant, which, when ignited, rapidly produces inflation gases under high pressure sufficient to inflate the associated airbag. The generated inflation gases are first directed through the filter for cooling and removal of any solid burning particulates therefrom prior to exiting the inflator, and are then directed to rupture the hermetic seal covering the inflator exit ports and next to pass out through the opened inflator exit ports into the open mouth of the folded airbag that surrounds the exit ports. This causes the airbag to expand and deploy in a matter of milliseconds out of the hidden vehicle compartment towards the occupants, i.e., driver and/or passengers. The inflated airbag provides a protective cushion that restrains the driver or passengers against various impact conditions with the interior of the vehicle.

In the manufacture of airbag inflators, it is prudent to inspect the inflators for proper construction prior to installation in the vehicle. It is well known that a single defect in the inflator construction, such as having a missing part, for instance, missing the gas generant, if gone undetected prior to installation, could cause the inflator not to fire when activated. This, in turn, could result in the airbag failing to inflate and deploy, leading to possible catastrophic injuries to vehicle occupants.

To insure that an essentially defect free inflator is produced, x-ray inspection devices have been employed in the automated inflator assembly lines in order to inspect assembled airbag inflators for missing parts and defects prior to being packaged for shipment. One type of prior x-ray inspection device for airbag inflators includes a lead-lined cabinet defining a central interior chamber that comprises a central interior space and entry and exit tunnel regions located on opposite sides of the central space. A conveyor belt passes through the entry and exit regions of the cabinet into the interior chamber for transporting the part to be inspected into the x-ray cabinet. Housed within the interior chamber is a standard x-ray source for directing an x-ray beam over the part to be inspected, a standard fluoroscopic screen located so as to receive the x-ray beam and convert it into visible radiation, and a standard visual imaging system for transmitting the visible radiation to a viewer.

The prior inflator inspection device is also equipped with automatic entry and exit doors that prevent the escape of physiologically harmful x-rays into the surrounding area and the consequent irradiation of personnel in this area by the escaping x-rays. The prior inflator inspection machine includes two banks of doors on each side of the x-ray cabinet disposed across the entry and exit tunnel regions. Each bank of doors is made up of two halves which open and close in a scissor type motion. In particular, each door half is generally triangular in shape and is pivotally suspended from a common pivot joint down across the opening provided in the entry and exit tunnel regions. When the halves are joined together, a seal is formed across the opening in the tunnel region, whereas when the halves are pivotally separated in opposite outward directions, an unobstructed opening is provided for the inflator to pass through. However, there are many shortcomings associated with the use of these double sets of entry and exit doors.

One drawback is that in order to meet federal regulatory agency requirements, any x-ray cabinet door that opens and closes and that exceeds 0.5 mRads of radiation leakage when open is required to have a primary safety interlock connected thereto that will immediately shut off the x-ray system when the door is open. The prior x-ray inspection machine falls in this category and, therefore, must either shut off each time the double doors open for a part to enter or exit the cabinet, which leads to increased inspection time, energy requirements and costs, or one of the two doors on each side of the cabinet must remain closed at all times in order to allow the x-ray system to remain on continuously, which increases the complexity of the operating system as well as leads to increased cycle time and reduced throughput.

For example, in the continuous operation mode, a part entering the cabinet first passes through the opened entry door, while the second entry door remains closed. The first door then closes behind the part and the second door thereafter opens to allow the part to enter the x-ray cabinet. After x-ray inspection, the part exits the other side of the cabinet in a similar fashion. This multi-stage operation tends to increase the inflator inspection time, reducing the throughput and lowering the operating efficiencies. Furthermore, to provide for continuous operation without having the possibility of radiation leakage from the x-ray cabinet during inflator transfer, each of the four scissor doors require two position sensors to indicate which of the two positions the door is in, either opened or closed, and a safety interlock to shut off the x-ray source if the door remains open when it should be closed, for a total of twelve costly switches that have to make or break contact at any given time. With all of the moving door parts and switches, problems invariably occur which create excessive downtime for adjustments. For instance, the moving door parts tend to malfunction and remain open from time to time, thereby automatically shutting off the x-ray system and causing expensive downtime and maintenance. Malfunctioning of the position sensors and safety interlocks also results in expensive downtime and maintenance and sometimes allows harmful x-rays to inadvertently escape from the x-ray cabinet.

It would be desirable to provide an x-ray inspection apparatus for airbag inflators that includes entry and exit doors that are much simpler in construction, less costly, contain a minimal number of moving parts and switches, are more reliable in operation, and provide improved shielding of system personnel from physiologically harmful radiation.

Different types of x-ray inspection apparatus have been proposed for inspecting various articles at airports, for instance, carrying-on baggage, that include shielded enclosures, closed by x-ray impermeable, hanging rigid doors or hanging flexible curtains, to prevent airport security personnel and passengers from exposure to harmful radiation.

U.S. Pat. No. 4,020,346 to Dennis discloses an x-ray machine for inspection of carry-on baggage at airports. The machine comprises a lead-shielded housing positioned over a conveyor belt. The housing defines an interior chamber having spaced apart entrance and exit openings and an intermediate central x-ray region. The device further includes two banks of spaced apart layers of flexible lead-shielded, vertically-slit, entrance and exit curtains on each side of the housing respectively covering the entrance and exit openings. The curtains conform to the shape of the carry-on baggage passing therethrough, thereby retarding the escape of x-rays from the machine while permitting the carry-on baggage to be conveyed through the machine.

U.S. Pat. No. 4,239,969 to Haas et al. discloses a similar airport carry-on baggage x-ray inspection machine. The x-ray machine includes two rows of spaced apart flexible, x-ray shielded, hanging curtains pivotally attached to the top wail of the entry and exit tunnel regions on each side of the x-ray impermeable housing, to prevent escape of stray radiation when the baggage passes through the tunnel into the central x-ray region. The curtains are spaced apart such that at least one of the curtains of the entrance and exit ports is always closed upon moving of the baggage through the x-ray chamber.

It is, however, undesirable to close entry and exit ports of an x-ray inspection machine for airbag inflators with hanging lead-lined flexible curtains. Because of the high number of inflators that are processed on a daily basis through an airbag inflator inspection machine, flexible curtains rapidly wear and pieces of the curtains constantly break off without notice to the operator. Broken curtains leave the operator unknowingly exposed to x-ray leakage. In addition, there is no guarantee that the curtains will remain closed during operation. An object may inadvertently block the curtain so that it remains open, which, in turn, would expose the operator to harmful radiation.

Another type of carry-on baggage x-ray inspection apparatus is disclosed in U.S. Pat. No. 4,879,735 to Owens. The airport inspection machine includes a single entry door comprising a pivotal rigid baffle pivotally suspended from the upper edge of the inlet opening to the x-ray cabinet to a preselected distance above the conveyor. Consequently, the entry door covers only an upper region of the entry port to the x-ray cabinet, leaving an opened space adjacent the conveyor for unobstructed passage of a horizontally placed piece of baggage. The machine also presumably includes a permanently opened exit port having no door. For the obvious reasons, this x-ray inspection machine could not be used to safely inspect airbag inflators, since the entry and exit ports remain opened at all times, resulting in constant leakage of harmful radiation from the machine into the surrounding area.

Certain kinds of revolving doors have also been proposed for use in devices that transfer articles between "clean" and "contaminated" environments. Such revolving doors are generally included to provide shielding against cross-contamination of the separated atmospheres during the transfer operations. However, rotary doors of any kind have not heretofore been taught or suggested for use in connection with an article x-ray inspection apparatus, and, in particular, to one which inspects airbag inflators.

U.S. Pat. No. 925,605 to Solliday discloses a device for transferring ice-cream cans to and from a cooling room without escape of cold air during operation. The device includes an entrance tunnel covered by an outwardly swinging hinged door. Positioned inside the tunnel housing between the entrance port to the cool room and the outer hinged door is an enclosed revolving door that comprises two right-angled partition walls mounted between a disc-shaped turntable roof and floor. The ice cream cans are placed on the turntable floor between adjacent partition openings and then the turntable is rotated while the outer edges of the partition walls engage the walls of the entrance tunnel to prevent the escape of cold air.

U.S. Pat. No. 4,205,216 to Douglas discloses a laser welding machine having a housing formed with an opening through which a work piece is passed into the laser welding station located inside the machine. A rotatable disc-shaped turntable is mounted to a drive shaft above stationary base. A set of radially spaced apart, light impermeable, sheet metal baffles extending radially outward from a central hub, are mounted uprightly atop the turntable. The turntable is centrally positioned and sealingly mounted in the opening of the housing. Flexible end portions mounted on the ends of the baffles engage the housing walls as the turntable is rotated within the housing. The work piece to be welded is placed between adjacent baffles along the outer periphery of the turntable and then rotated into the welding station for welding, while the baffles and flexible end portions inhibit harmful laser radiation from exiting the housing and irradiating the system operator.

Thus, in both of the aforesaid U.S. Pat. No. 925,605 to Solliday and U.S. Pat. No. 4,205,216 to Douglas, the type of rotating door that is disclosed includes a revolving door where articles are positioned along the outer periphery of the door between radially extending wall partitions that have end portions engageable with the side walls of the housing, to provide a seal as the revolving door is rotated to effect article transfer.

U.S. Pat. No. 5,131,797 to Christiansen et al. discloses another type of transfer device to transport radiological swipes and smears between a clean environment and a contaminated environment without an open breach of containment. The transfer device includes an inner hollow rotatable cylinder rotatably disposed inside a fixed outer hollow cylinder housing. The inner cylinder contains two longitudinally spaced apart ports at opposite ends of the cylinder sidewall that both lead into the hollow interior cavity of the cylinder. The first port is provided in communication with a clean environment and the second port is provided in communication with a separated, contaminated environment. The centers of the ports are offset about 120° to allow one port to be opened at a time. The fixed outer cylinder housing has two center aligned, longitudinally spaced apart openings at opposite ends of the outer cylinder sidewall. The first opening is provided in communication with the clean environment and the second opening is provided in communication with the separated, contaminated environment. The first and second inner cylinder ports and first and second outer cylinder openings are respectively alignable with each other at different relative positions so as to allow communication between only one environment and the interior of the inner cylinder at a time.

In operation, the inner cylinder is rotated to a first position so that the first port thereof is coextensive with the first opening of the outer cylinder housing, while the second port remains closed. In this position, an article to be transferred from the clean environment can be placed inside the interior of the inner cylinder. Thereupon, the inner cylinder is rotated until the second port thereof is coextensive with the second opening of the outer cylinder housing, while the first port is closed, thereby establishing communication of the interior of the inner cylinder with the contaminated environment and enabling removal of the article from the interior of the cylinder into the contaminated environment.

The aforesaid door assembly of Christiansen would be undesirable for many reasons in an airbag inflator x-ray inspection device. For instance, the inclusion of longitudinally spaced entry and exit ports formed in a single inner cylinder would make the inflator conveyor system extremely complicated and require multiple conveyor belts. Furthermore, such a transfer system would not be economical and practical for a conveyor fed airbag inflator x-ray inspection system due to its complexity.

What is needed is a new and improved x-ray inspection apparatus for inspecting articles, especially assembled airbag inflators, having new and improved rotating entry and exit door assemblies that are much simpler in construction, contain a minimal number of moving parts and switches, are more reliable in operation, reduce cycle time and increase inflator throughput, and provide improved shielding of system personnel from physiologically harmful radiation.

SUMMARY OF THE INVENTION

It is an object of this invention, therefore, to provide a new and improved x-ray inspection apparatus for inspecting various articles, especially airbag inflators, without suffering from the foregoing disadvantages associated with conventional airbag inflator x-ray inspection machines.

It is a related object of this invention to provide new and improved entry and/or exit doors for an airbag inflator x-ray inspection apparatus.

It is another object of this invention to provide rotating entry and exit doors for an airbag inflator x-ray inspection apparatus that have improved radiation shielding structures to better prevent x-rays from exiting the apparatus and harmfully irradiating line personnel.

It is yet another object of this invention to provide rotating entry and exit doors for an airbag inflator x-ray inspection apparatus that are much simpler in construction and more reliable in performance.

It is still another object of this invention to provide rotating entry and exit doors for an airbag inflator x-ray inspection apparatus that reduce cycle time and increase inflator throughput and overall system efficiency.

And still another object of this invention is to provide rotating entry and exit doors for an airbag inflator x-ray inspection apparatus that reduce the number of position sensors and eliminate the need for safety interlocks.

Yet still a further object of this invention is to provide rotating entry and exit doors for an airbag inflator x-ray inspection apparatus that seal x-rays within the apparatus in all rotative positions to allow for continuous operation of the x-ray apparatus without the potential of the doors being in a position where x-rays could exit the apparatus during continuous operation.

In accomplishing these and other objects, features and advantages of this invention, this invention resides in one aspect in an article, especially an airbag inflator, x-ray inspection apparatus, which comprises: an x-ray impermeable housing defining an interior chamber having spaced apart entry and exit openings and an x-ray inspection section intermediate thereto; an x-ray source disposed inside the interior chamber and positioned so as to direct x-ray beams at an article in the inspection section; a visual imager disposed inside the interior chamber and positioned so as to receive the x-ray beams and convert the x-ray beams into a visual image; a conveyor extending through the entry and exit openings and the inspection section to transport the article into and out of the interior chamber; and, motorized rotatable entry and exit doors rotatably mounted respectively across the entry and exit openings to substantially prevent escape of x-ray beams from the interior chamber to an exterior of the housing while permitting the article to be conveyed into and out of the interior chamber, each rotatable door comprising an x-ray impermeable rotatable cylindrical drum having a hollow interior cavity and one opening along a sidewall thereof leading into the interior cavity, the one drum opening being generally configured to receive the article, the one drum opening being rotatably alignable in a first position so as to enable open communication between the exterior of the housing and the interior cavity in the drum, and the one drum opening being rotatably alignable in a second position so as to enable open communication between the interior chamber and the interior cavity in the drum.

The various objects, features and advantages of this invention will become more apparent from the following description and appended claims.

BRIEF DESCRIPTION OF THE DRAWINGS

There are shown in the drawings certain exemplary embodiments of the invention as presently preferred. It should be understood that the invention is not limited to these embodiments and is capable of variation within the spirit and scope of the appended claims.

With this description of the invention, a detailed description follows with reference to the drawings, in which like reference numerals denote like elements, and in which.

DETAILED DESCRIPTION OF THE PREFERRED EMBODIMENTS OF THE INVENTION

The present invention provides a new and improved x-ray inspection apparatus for inspecting various articles, and, in particular, for inspecting assembled airbag inflators for defects in construction. The x-ray inspection apparatus contains new and improved rotary entry and exit door assemblies that provide for the inflator parts traveling on a conveyor to enter and exit the inspection apparatus without leakage of x-rays and consequent irradiation of persons in the surrounding area. In every position the improved door assemblies prevent x-rays from exiting the x-ray inspection apparatus. This feature advantageously allows the x-ray machine to be operated in a continuous mode without the potential of the doors ever being in a position for x-rays to escape. Each door includes a single rotatable hollow cylindrical drum rotatably connected to both an entrance and exit port of the apparatus, in which the cylindrical drum door has only one opening leading into the interior of the drum for passage of an inflator therein and can be rotated to be in open communication with either the exterior or interior of the inspection apparatus to effect transfer.

Figure 1:
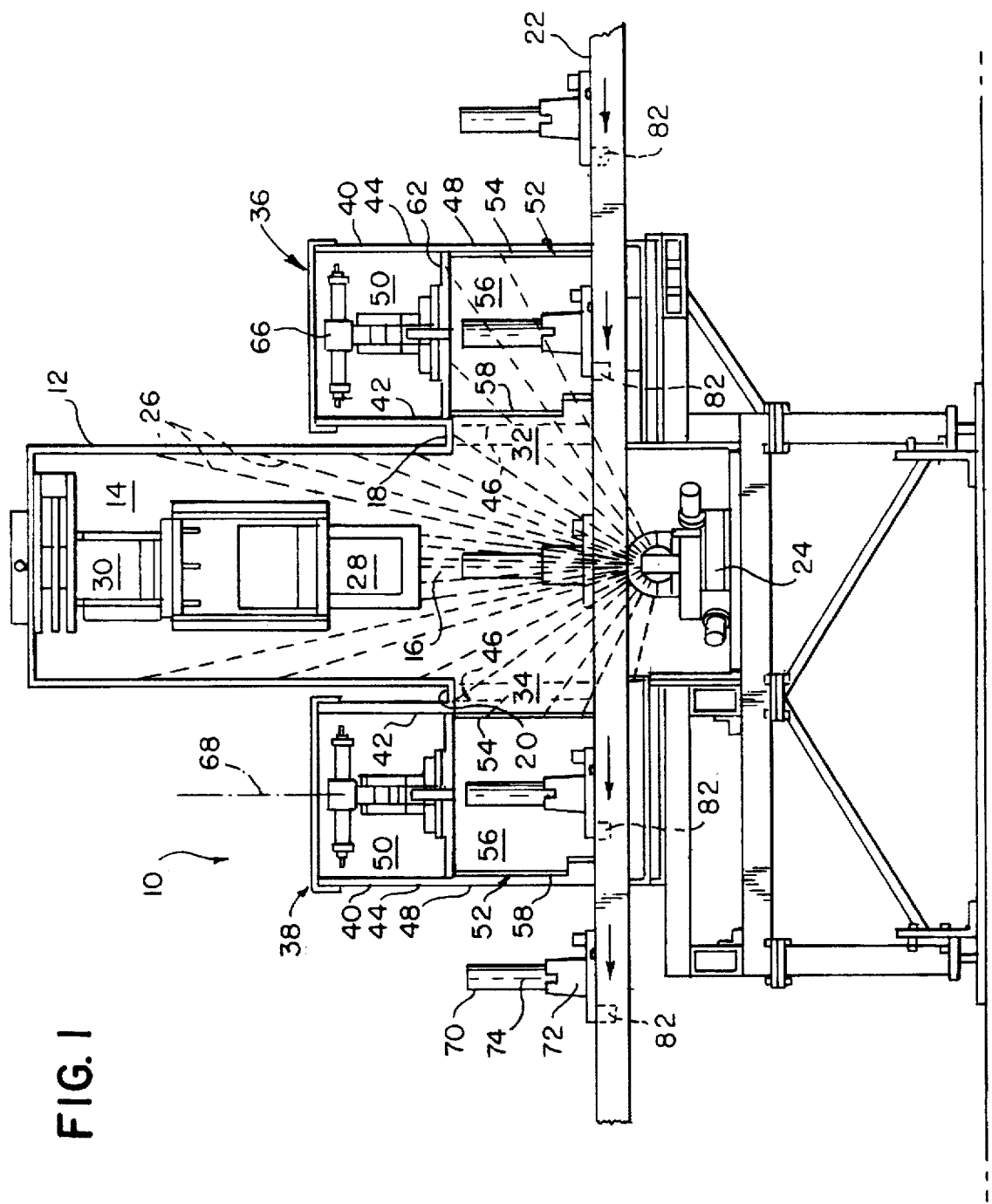
FIG. 1 is a sectional front view of an airbag inflator x-ray inspection apparatus having rotating entry and exit doors in accordance with the present invention.

Referring now to FIG. 1 of the drawings, the x-ray inspection apparatus 10 of the present invention includes an x-ray impermeable, e.g., lead-lined, cabinet enclosure 12, preferably composed of steel, that defines an interior chamber 14. The interior chamber 14 comprises a central inspection space 16 and entry and exit sections 18 and 20 located on opposite sides of the central space 16. A motorized conveyor belt 22 passes through the entry and exit sections 18 and 20 and through the central space 16 intermediate thereto for transporting the part to be inspected into the x-ray cabinet 12. The conveyor belt 22 traveling to and from the x-ray inspection apparatus may form a portion of an automated airbag inflator assembly line (not shown).

Housed inside the x-ray cabinet 12 in the central inspection station 16 is a standard x-ray source 24 for directing x-ray beams 26 over the part to be inspected, a standard fluoroscopic screen 28 located so as to receive the x-ray beams 26 and convert the x-radiation into visible radiation, and a standard visual imaging system 30 for transmitting the visible radiation to a viewer and/or to a computer that records and compares the x-rayed image of the inspected part with a standard part stored in memory. As shown in FIG. 1, the x-ray source 24 is located underneath the conveyor belt 22, while the fluoroscope 28 and visual imaging system 30 are suspended from the top of the x-ray cabinet 12 down to a distance spaced above the conveyor belt 22, leaving enough space for the part to be inspected to pass thereunder. It should be understood that x-ray imaging techniques other than an x-ray fluoroscopy may be practiced in accordance with the present invention, such as real time x-ray radiography and other well known techniques.

The entry and exit sections 18 and 20 define enclosed passageways that have respective entry and exit openings 32 and 34, so as to allow the part traveling on the conveyor 22 to enter and exit the interior chamber 14 of the cabinet 12. Respectively positioned adjacent to each of the entry and exit openings 32 and 34 are entry and exit rotating door assemblies 36 and 38 of the present invention that are provided to seal emitted x-radiation inside the interior chamber 12 and prevent x-radiation from exiting the cabinet 12, even during continuous operation, to the surrounding outer area and exposing line personnel to harmful radiation.

Figure 2:
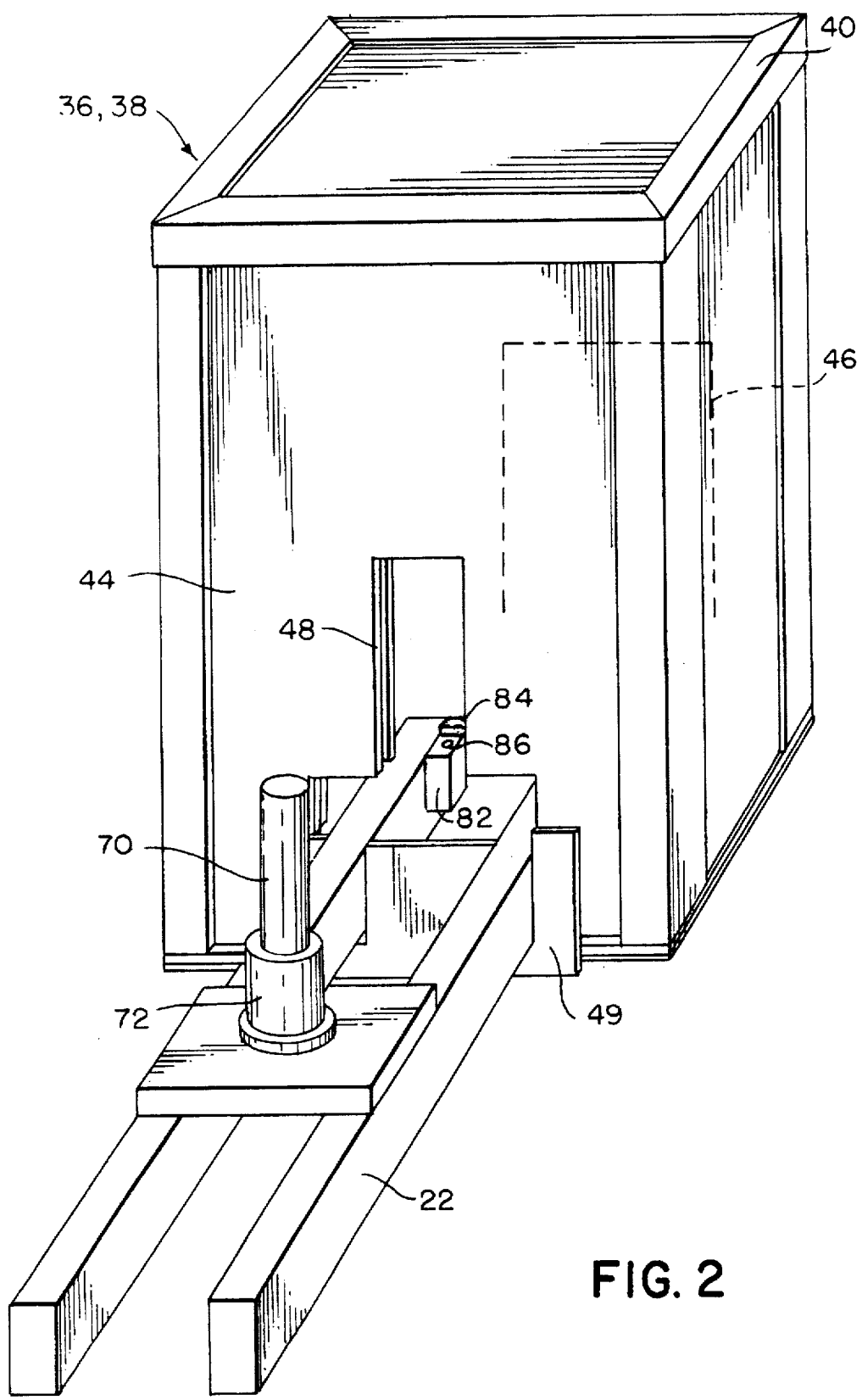
FIG. 2 is a-side view of the entry or exit door cabinet that is disposed adjacent to respective entry and exit sections of the x-ray inspection apparatus of FIG. 1, each door cabinet respectively .housing a rotating entry or exit door.
Figure 3:
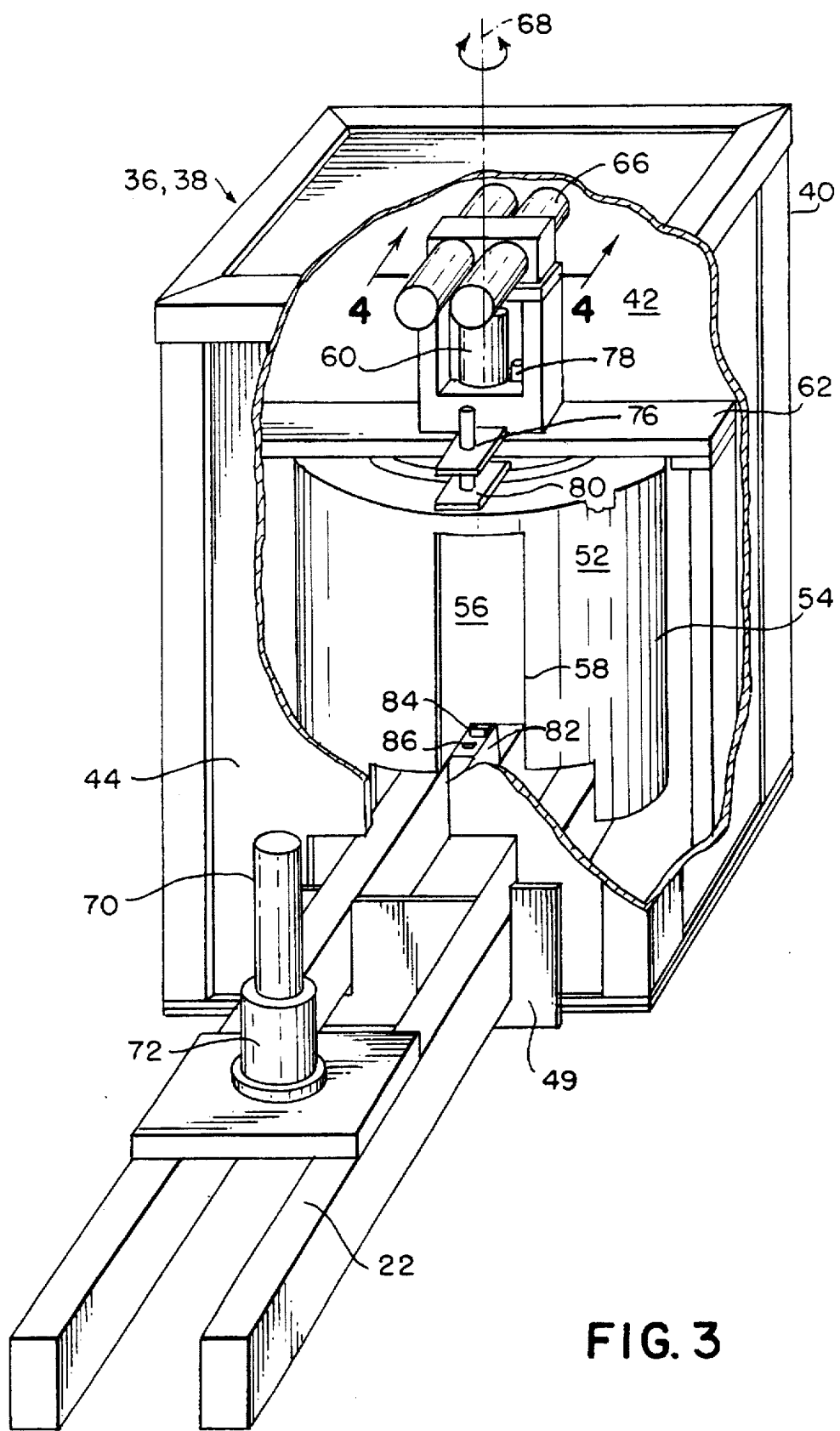
FIG. 3 is a side view of the entry or exit door cabinet of FIG. 2, partially cutaway, showing the rotating entry or exit door housed therein.
Figure 4:
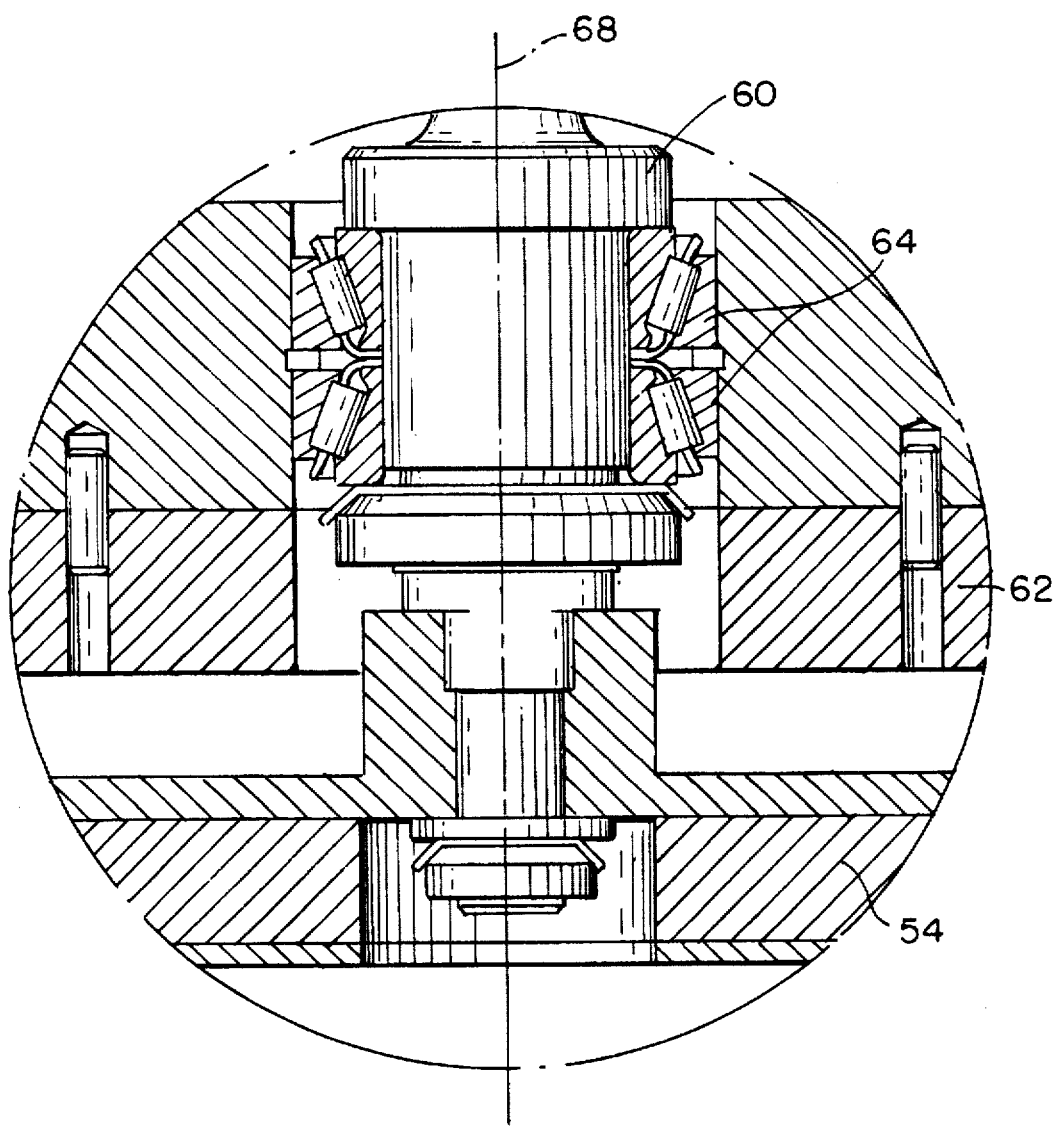
FIG. 4 is a fractional view taken along line 4—4 of FIG. 3, showing the rotational mounting assembly of the rotating door in the door cabinet.

As illustrated in FIGS. 1–3, each rotating door assembly 36, 38 includes an x-ray impermeable, e.g., lead-lined, door cabinet 40 enclosure, preferably composed of steel, that includes two spaced apart opposed side walls 42 and 44. The inner side wall 42 of both the entry and exit door assemblies 36 and 38 is located adjacent to respective exit and entry openings 32 and 34 in the x-ray cabinet 12, and the outer side wall 44 is disposed more remote from the exit and entry openings 32 and 34. Each side wall 42 and 44 includes respective openings 46 and 48 that are generally configured to allow the part traveling on the conveyor 22 to pass therethrough. An x-ray impermeable, e.g., lead-lined, shield 49 is placed below the opening 48 to prevent x-ray leakage between the conveyor belt 22. The door cabinet 40 defines an interior chamber 50 intermediate to the side walls 42 and 44 which houses a rotatable door 52. Although the door cabinet 40 is shown in the drawings as being a separate module, it should be understood that the door cabinet may also be formed as one-piece with the x-ray cabinet.

Figure 5:
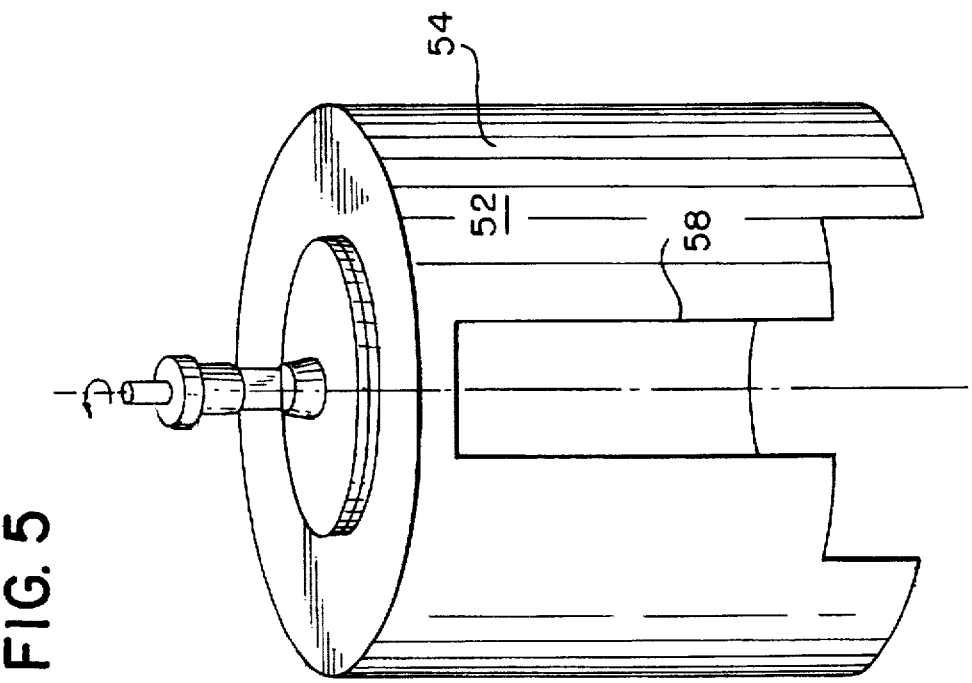
FIG. 5 is a perspective view of a rotating entry or exit door of the x-ray inspection apparatus of FIG. 1 shown in an first rotative position; and, FIG. 6 is a perspective view of a rotating entry or exit door of the x-ray inspection apparatus of FIG. 1 shown in a second rotative position.
Figure 6:
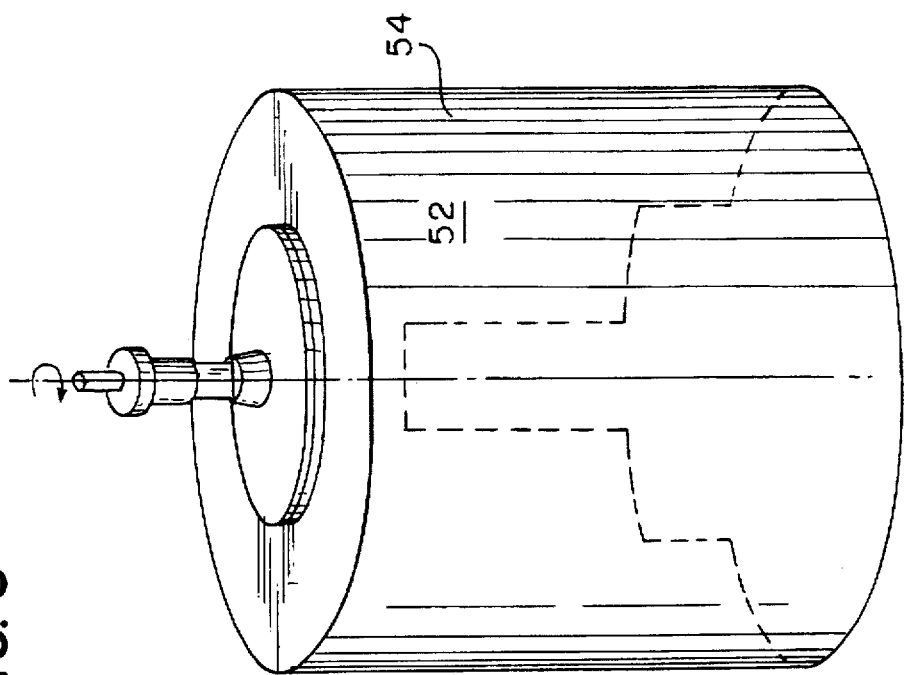

Referring now to FIGS. 1 and 3–6, the rotatable door 52 comprises an x-ray impermeable, e.g., lead-lined, rotatable cylindrical drum 54, preferably composed of stainless steel for enhanced x-ray shielding, that defines a hollow interior cavity 56. The drum 54 includes a closed top wall, an opened bottom spaced immediately above the conveyor 12, and a circumferential side wall. The drum 54 contains only one opening 58 formed along a selected portion of its circumferential side wall to define a door leading into the hollow interior cavity 56. The drum door is also configured, as are the door cabinet openings 46 and 48, to allow a part traveling on the conveyor 22 to pass therethrough. The drum 54 also includes a shaft 60 centrally mounted on the top wall of the drum. The shaft 60 is rotatably mounted to a support bridge 62 and coupled to bearings 64 (FIG. 4) and also to a standard pneumatic rotary actuator 66 which drives the shaft and causes rotation along a generally vertical rotational axis 68. It should be understood that other well known drive means may also be used to rotate the shaft 60, although it is preferred to use a pneumatic rotary actuator which is simple construction and requires low maintenance. As shown in FIGS. 5 and 6, the cylindrical drum 54 is set up to rotate back and forth between two rotative positions that are preferably spaced about 180° apart.

In accordance with the present invention, only one rotating door assembly 36 containing one rotatable cylindrical drum 54 is disposed adjacent to the entry port 32 of the x-ray cabinet 12 and only one rotating door assembly 38 containing one rotatable cylindrical drum 54 is likewise disposed adjacent to the exit port 34 of the x-ray cabinet.

Referring again to FIGS. 1–3, the part to be x-ray inspected is shown to be an assembled airbag inflator 70. The inflator 70 is positioned upright on its end in a pallet 72 which is used to correctly position the inflator 70 and to stably transport the inflator through the x-ray inspection apparatus 10. It should be understood that other types of parts to be inspected can be used in accordance with the present invention, for example, carry-on baggage at airports.

The airbag inflator 70 may be of any well known type including well known pyrotechnic, hybrid, fluid fuel inflators for vehicle driver side, passenger side, and side impact applications. The inflator 70 shown in the drawings for illustrative purposes is a standard passenger side pyrotechnic inflator which generally comprises, if assembled correctly, an elongated cylindrical body 74 having ignition squib (not shown) disposed at one end of the body in communication with a central perforated igniter tube (not shown) containing a pyrotechnic and a rapid deflagration cord that runs between the opposite ends of the body along a longitudinal axis. Generally surrounding the central igniter tube is a gas generant wafer pack (not shown) containing stacked pyrotechnic washer-shaped wafers. Generally surrounding the pyrotechnic wafer pack is a filter pack (not shown) formed of screens and/or porous ceramic bodies. The inflator body is externally ported (not shown) to define gas exit ports for venting of generated gases into an associated airbag upon activation. The exit ports are initially sealed with a frangible foil liner (not shown).

The airbag inflator x-ray inspection apparatus 10 is operated as follows. First the opening 58 on the rotatable drum 54 of the rotating entry door assembly 36 is positioned upstream coincident with the opening 48 in the door cabinet 40 to receive an airbag inflator 70 traveling on the conveyor 22. The inflator is caused to enter the opening 58 in the drum door 54 and travel into the hollow interior cavity 56 thereof, where the inflator is momentarily stopped therein. The rotatable drum 54 of the entry door assembly 36 is then rotated 180°, so that the door opening 58 is positioned downstream (as shown in FIG. 1) coincident with the opening 46 in the door cabinet 40. In this position, the interior cavity 56 of the drum is provided in open x-radiation communication with the interior chamber 14 of the x-ray cabinet 12.

Next the inflator 70 is caused to exit from the door opening 46 and travel through the entry section 18 of the x-ray cabinet 12 until it reaches the central inspection section 16, where again the inflator 70 is caused to stop momentarily. The inflator 70 is then x-rayed as the x-ray beam 26 passes therethrough. As described previously, it is preferred to operate the x-ray beam 26 continuously without turning the x-ray source 24 off. The continuous operation reduces cycle time for inspecting an inflator, thereby increasing inflator throughput and leading to greater operating efficiencies.

After the inflator 70 is x-ray inspected, the cylindrical drum 54 of the rotating exit door assembly 38 is positioned upstream so that the drum opening 58 is coincident with the opening 46 in the door cabinet 40. In this position, the interior cavity 56 of the drum is provided in open x-radiation communication with the interior chamber 14 of the x-ray cabinet 12. The inspected inflator 70 is caused to exit the exit section 20 of the x-ray cabinet 12 and then enter the door opening 58 in the rotatable drum 54 of the exit door assembly 38 and travel into the interior cavity 56 thereof, where again the inflator is stopped momentarily.

The rotatable drum 52 of the exit door 38 is then caused to rotate 180°, so that the drum door opening 58 is in the downstream position (as shown in FIG. 1) coincident with the opening 48 in the x-ray cabinet 12. The inflator is then caused to pass out through the door cabinet opening 48 and, if approved after inspection, is allowed to continue along the conveyor 22 to the next operation. Multiple inflators 70 can be spaced apart along the conveyor as shown in FIG. 1 to allow for rapid and efficient inspection.

In a preferred embodiment as shown in FIG. 3, each rotatable door 52 includes two standard position sensors 76 and 78 mounted on the support bridge 62. The position sensors 76 and 78 are spaced about 180° apart and are respectively positioned coincident with openings 48 and 46 formed in the door cabinet 40. A counterpart metal flag 80 is mounted to the top of the rotatable drum 54 above the drum door opening 58. The two position sensors 76 and 78 and metal flag 80 are used to indicate which of the two rotative positions the cylindrical drum 54 is in at any given time, either upstream or downstream.

Also in a preferred embodiment as shown in FIGS. 1–3, the momentary stoppage of the air bag inflator 70 during operation of the x-ray inspection apparatus 10 is caused by having spaced apart pallet stops 82 positioned at desired locations along the conveyor line 22. It is preferred to operate the conveyor 22 continuously which, therefore, requires mechanical stops to halt the progress of the inflators 70 traveling thereon. A pallet stop 82 includes a movable plunger 84 which hinges up and down. In the up position, the plunger 84 is caused to engage the leading edge of a pallet 72 to stop its progress. In the down position, the pallet 72 carrying the inflator 70 is released and allowed to travel along the conveyor 22. A position sensor 86 is mounted on each pallet stop 82 and a counterpart metal flag (not shown) is mounted underneath the front edge of the pallet 72 to indicate whether a pallet is over the pallet stop 82.

The upstream and downstream positioning of the rotatable doors 52 and the up and down positioning of the pallet stops 82 can be synchronized using their respective position sensors, such that when the drum door 54 rotates, the plunger 84 in the pallet stop 82 will drop to release a pallet 72 and then return back up to be in a position ready to engage another pallet 72 traveling behind the released pallet 72. The pallet stop 82 can also be programmed not to release its pallet 72 until the pallet stop 82 in front of it has released its pallet 72 and is clear to receive the next pallet.

Referring again to FIG. 1, the continuously on x-ray beams 26 cannot escape through the drum 54 of the rotating entry or exit door 36 or 38 into the surrounding area outside the x-ray inspection apparatus 10 during and in between transfer operations. As shown, when the rotatable drum 54 of the entry door 36 is in the downstream position, the inside of the cylindrical side wall opposite the drum opening 58, that is preferably lead-lined, effectively stops the x-radiation from exiting the apparatus. Furthermore, x-radiation travels in a straight line and cannot travel through a curved path. Consequently, the x-radiation travel around the external periphery of the side wall and escape through the cabinet door opening 48. The same shielding effect would occur when the rotatable drum 54 of the exit door 38 is in the upstream position (not shown).

Also as shown in FIG. 1, when the rotatable drum 54 of the exit door 38 is positioned in the downstream position, the external, preferably stainless steel, periphery of the cylindrical side wall opposite the drum opening 58 effectively blocks the x-radiation from exiting the apparatus. Furthermore, x-radiation travels in a straight line and cannot travel through a curved path. Consequently, the x-radiation travel around the external periphery of the side wall and escape through the cabinet door opening 48. The same is true when the drum 54 of the entry door 36 is positioned in the upstream position (not shown).

Accordingly, no matter what position the rotating cylindrical drum door is in, either up stream, downstream, and passing intermediate positions thereto, x-radiation is blocked from exiting the x-ray inspection apparatus into the surrounding area. Accordingly, this type of rotating door of the present invention effectively seals x-radiation from exiting the apparatus in all rotative positions, which provides better shielding of line personnel from harmful radiation and also allows the x-ray source to remain on at all times without the possibility of x-radiation escaping. The new and improved rotating entry and exit doors also significantly reduce the number of doors required to operate the apparatus safely and continuously, the number position sensors, and the number of moving parts and wear areas associated therewith which can lead to excessive downtime. These doors also reduce cycle time which increases the number of parts processed through the apparatus as well as eliminate altogether the need for safety interlocks. All the aforesaid factors lead to a new and improved airbag inflator x-ray inspection apparatus that is safer, simpler, more reliable, requires less maintenance and has improved operating efficiencies.

The invention having been disclosed in connection with the foregoing embodiments and variations, other embodiments of the invention will be apparent to persons skilled in the art. The invention is not intended to be limited to the embodiments and variations disclosed, which are considered to be purely exemplary. Accordingly, reference should be made to the appended claims to assess the true spirit and scope of the invention, in which exclusive rights are claimed.

The subject matter claimed is:

1. An article x-ray inspection apparatus, which comprises:

an x-ray impermeable housing defining an interior chamber having spaced apart entry and exit openings and an x-ray inspection section intermediate thereto;

an x-ray source disposed inside said interior chamber and positioned so as to direct x-ray beams at an article in said inspection section;

a visual imager disposed inside said interior chamber and positioned so as to receive said x-ray beams and convert said x-ray beams into a visual image;

a conveyor extending through said entry and exit openings and said inspection section to transport said article into and out of said interior chamber; and, rotatable entry and exit doors rotatably mounted respectively across said entry and exit openings to substantially prevent escape of x-ray beams from the interior chamber to an exterior of said housing while permitting said article to be conveyed into and out of said interior chamber, each rotatable door comprising an x-ray impermeable rotatable drum having a hollow interior cavity and one opening along a sidewall thereof leading into said interior cavity, said one drum opening being generally configured to receive said article, said one drum opening being rotatably alignable in a first position so as to enable open communication between said exterior of said housing and the interior cavity in said drum, and said one drum opening being rotatably alignable in a second position so as to enable open communication between said interior chamber and the interior cavity in said drum.

2. The apparatus of claim 1, in which said article is an airbag inflator.

3. The apparatus of claim 1, in which said drum is cylindrical.

4. The apparatus of claim 1, in which said x-ray impermeable housing comprises a lead-lined metal housing.

5. The apparatus of claim 1, in which said x-ray impermeable drum comprises a lead-lined metal drum.

6. The apparatus of claim 1, in which said rotatable door comprises a cylindrical drum having a closed top wall, an open bottom wall, and a side wall with one opening.

7. The apparatus of claim 6, in which a motorized shaft is mounted to said top wall of said drum to drive said drum between said two rotative positions.

8. The apparatus of claim 1, in which said x-ray source continuously operates without having x-ray beams escape from the interior chamber during article transfer in and out of said interior chamber.

9. The apparatus of claim 1, in which said visual imager comprises a fluoroscopic screen to receive and convert said x-ray beams to a visual image and an visual imaging monitor to display said images for detection of defects.

10. An article x-ray inspection apparatus, which comprises:

an x-ray impermeable housing defining an interior chamber having spaced apart opened entry and exit sections and an x-ray inspection section intermediate thereto;

an x-ray source disposed inside said interior chamber and positioned so as to direct x-ray beams at an article in said inspection section;

a visual imager disposed inside said interior chamber and positioned so as to receive x-ray beams and convert said x-ray beams into a visual image;

a conveyor extending through a lower portion of said entry and exit sections and a lower portion of said inspection section to transport said article into and out of said interior chamber; and, motorized rotatable entry and exit doors respectively closing said opened entry and exit sections to substantially prevent escape of x-ray beams from the interior chamber to an exterior of said housing while permitting said article to be conveyed into and out of said chamber, each rotatable door comprising an x-ray impermeable door housing mounted to respective opened entry and exit sections, said door housing having two spaced opposed side walls, each side wall having one opening configured to receive said article therethrough and having said conveyor extend through a lower portion thereof, one of said opposed side walls being disposed across said respective entry and exit sections and the other of said opposed side walls being disposed more remote from said entry and exit sections, and a rotatable drum door rotatably mounted between said opposed side walls across said openings thereof, said drum door being positioned immediately above said conveyor, said rotatable drum door comprising an x-ray impermeable rotatable drum having a hollow interior cavity and one opening along a sidewall thereof leading into said interior cavity, said one drum opening being generally configured to receive said article therethrough, said one drum opening being rotatably alignable in a first position coincident with said one of said two opposed side wall openings in said door housing so as to enable open communication between said exterior of said housing and the interior cavity in said drum, and said one drum opening being rotatably alignable in a second position coincident with said other of said two side wall openings in said door housing so as to enable open communication, between said interior chamber and the interior cavity in said drum.

11. The apparatus of claim 10, in which said article is an airbag inflator.

12. The apparatus of claim 10, in which said drum is cylindrical.

13. The apparatus of claim 10, in which said x-ray impermeable housing comprises a lead-lined metal housing.

14. The apparatus of claim 10, in which said x-ray impermeable door housing comprises a lead-lined metal housing.

15. The apparatus of claim 10, in which said x-ray impermeable drum comprises a lead-lined metal drum.

16. The apparatus of claim 10, in which said rotatable door comprises a cylindrical drum having a closed top wall, an open bottom wall, and a side wall with one opening.

17. The apparatus of claim 16, in which a motorized shaft is mounted to said top wall of said drum to drive said drum between said two rotative positions.

18. The apparatus of claim 10, in which said x-ray source continuously operates without having x-ray beams escape from the interior chamber during article transfer in and out of said interior chamber.

19. The apparatus of claim 10, in which said visual imager comprises a fluoroscopic screen to receive and convert said x-ray beams to a visual image and an visual imaging monitor to display said images for detection of defects in construction.

20. The apparatus of claim 10, in which said first and second rotatable positions are about 180° apart.

21. A rotating door assembly for an article inspection apparatus, which comprises:

an x-ray impermeable enclosure defining an interior chamber having two spaced apart opposed side walls, each of said opposed side walls having one opening formed therein configured to receive an article;

a motorized rotatable drum door rotatably mounted in said interior chamber between said opposed side walls across said openings thereof;

said rotatable drum door comprising an x-ray impermeable rotatable drum having a hollow interior cavity and one opening along a sidewall thereof leading into said interior cavity, said one drum opening being generally configured to receive said article, said one drum opening being rotatably alignable in a first position coincident with said first side wall opening in said door enclosure so as to enable open communication between said exterior of said door enclosure and the interior cavity in said drum, and said one drum opening being rotatably alignable in a second position coincident with said other opposed side wall opening in said door enclosure so as to enable open communication between said opposed exterior of said door enclosure and the interior cavity in said drum; and, said rotating door assembly being mounted to entry port, exit port, or both of an article x-ray inspection apparatus.

22. The apparatus of claim 21, in which said first and second rotatable positions are about 180° apart.

* * * * *